United States Patent
Lee et al.

(10) Patent No.: US 9,261,485 B2
(45) Date of Patent: Feb. 16, 2016

(54) PROVIDING COLOR DOPPLER IMAGE BASED ON QUALIFICATION CURVE INFORMATION IN ULTRASOUND SYSTEM

(75) Inventors: Hyeong Do Lee, Seoul (KR); Jae Keun Lee, Seoul (KR)

(73) Assignee: SAMSUNG MEDISON CO., LTD., Hongcheon-Gun, Gangwon-Do (KR)

(*) Notice: Subject to any disclaimer, the term of this patent is extended or adjusted under 35 U.S.C. 154(b) by 156 days.

(21) Appl. No.: 13/298,779

(22) Filed: Nov. 17, 2011

(65) Prior Publication Data

US 2012/0130249 A1 May 24, 2012

(30) Foreign Application Priority Data

Nov. 23, 2010 (KR) .................. 10-2010-0116920

(51) Int. Cl.
| | |
|---|---|
| A61B 8/00 | (2006.01) |
| G01N 29/06 | (2006.01) |
| A61B 8/06 | (2006.01) |
| A61B 8/08 | (2006.01) |
| G01N 29/024 | (2006.01) |
| G01S 15/89 | (2006.01) |
| G01S 7/52 | (2006.01) |

(52) U.S. Cl.
CPC .............. *G01N 29/0654* (2013.01); *A61B 8/06* (2013.01); *A61B 8/488* (2013.01); *G01N 29/024* (2013.01); *G01S 15/8981* (2013.01); *G01N 2291/017* (2013.01); *G01N 2291/02466* (2013.01); *G01S 7/52071* (2013.01); *G01S 15/8988* (2013.01)

(58) Field of Classification Search
None
See application file for complete search history.

(56) References Cited

U.S. PATENT DOCUMENTS

| 4,911,171 A | * | 3/1990 | Uchibori | ......................... 600/455 |
| 4,932,415 A | * | 6/1990 | Angelsen et al. | ............. 600/455 |

(Continued)

FOREIGN PATENT DOCUMENTS

| JP | 4-218143 A | 8/1992 |
| JP | 2009-011711 A | 1/2009 |

(Continued)

OTHER PUBLICATIONS

European Search Report issued in European Application No. 11 18 9301 dated Oct. 18, 2013.

(Continued)

*Primary Examiner* — Nicholas Evoy
(74) *Attorney, Agent, or Firm* — McDermott Will & Emery LLP

(57) ABSTRACT

There are provided embodiments for providing a color Doppler image based on qualification curve information. In one embodiment, an ultrasound system comprises: an ultrasound data acquisition unit configured to acquire ultrasound data corresponding to a living body including a moving target object; a storage unit for storing qualification curve information for determining blood flow signals of the target object, clutter signals and noise based on velocity and power components of Doppler signals; and a processing unit configured to form first Doppler signals based on the ultrasound data, perform a clutter filtering process upon the first Doppler signals to form second Doppler signals, calculate velocity and power components of the second Doppler signals, form a color Doppler image based on the calculated velocity and power components, and perform a blending process upon the color Doppler image based on the calculated velocity and power components and the qualification curve information.

4 Claims, 4 Drawing Sheets

(56) References Cited

U.S. PATENT DOCUMENTS

| | | | | |
|---|---|---|---|---|
| 5,144,954 | A * | 9/1992 | Satake | 600/455 |
| 5,148,808 | A * | 9/1992 | Satake | 600/441 |
| 5,163,434 | A * | 11/1992 | Kumazawa | 600/455 |
| 5,190,044 | A * | 3/1993 | Kawasaki et al. | 600/455 |
| 5,718,229 | A * | 2/1998 | Pesque et al. | 600/441 |
| 5,720,291 | A | 2/1998 | Schwartz | |
| 5,931,784 | A * | 8/1999 | Kajiwara et al. | 600/441 |
| 6,036,643 | A * | 3/2000 | Criton et al. | 600/454 |
| 6,364,835 | B1 * | 4/2002 | Hossack et al. | 600/443 |
| 6,402,694 | B1 | 6/2002 | Bae et al. | |
| 6,511,426 | B1 * | 1/2003 | Hossack et al. | 600/437 |
| 6,524,249 | B2 * | 2/2003 | Moehring et al. | 600/438 |
| 6,547,736 | B1 * | 4/2003 | Moehring et al. | 600/454 |
| 6,554,770 | B1 * | 4/2003 | Sumanaweera et al. | 600/443 |
| 6,616,611 | B1 * | 9/2003 | Moehring | 600/454 |
| 6,641,536 | B2 * | 11/2003 | Hossack et al. | 600/443 |
| 6,679,843 | B2 * | 1/2004 | Ma et al. | 600/441 |
| 6,689,064 | B2 * | 2/2004 | Hager et al. | 600/454 |
| 6,733,455 | B2 * | 5/2004 | Mo et al. | 600/454 |
| 6,755,787 | B2 * | 6/2004 | Hossack et al. | 600/447 |
| 6,997,876 | B2 * | 2/2006 | Mo et al. | 600/455 |
| 7,128,713 | B2 * | 10/2006 | Moehring et al. | 600/453 |
| 7,425,198 | B2 * | 9/2008 | Moehring et al. | 600/454 |
| 7,537,568 | B2 * | 5/2009 | Moehring | 600/454 |
| 7,608,044 | B2 * | 10/2009 | Tanigawa | 600/441 |
| 7,713,204 | B2 * | 5/2010 | Sakaguchi et al. | 600/441 |
| 7,736,314 | B2 * | 6/2010 | Beach et al. | 600/437 |
| 7,771,358 | B2 * | 8/2010 | Moehring et al. | 600/454 |
| 7,837,624 | B1 * | 11/2010 | Hossack et al. | 600/443 |
| 8,425,422 | B2 * | 4/2013 | Srinivasan et al. | 600/443 |
| 8,500,646 | B2 * | 8/2013 | Kim et al. | 600/453 |
| 8,545,411 | B2 | 10/2013 | Bae et al. | |
| 2002/0091319 | A1 * | 7/2002 | Moehring et al. | 600/454 |
| 2002/0120195 | A1 * | 8/2002 | Hossack et al. | 600/443 |
| 2003/0069505 | A1 * | 4/2003 | Hager et al. | 600/454 |
| 2003/0097068 | A1 * | 5/2003 | Hossack et al. | 600/443 |
| 2003/0236460 | A1 * | 12/2003 | Ma et al. | 600/441 |
| 2004/0210289 | A1 * | 10/2004 | Wang et al. | 607/116 |
| 2005/0033174 | A1 * | 2/2005 | Moehring et al. | 600/453 |
| 2005/0075568 | A1 * | 4/2005 | Moehring | 600/453 |
| 2005/0101863 | A1 * | 5/2005 | Kawagishi et al. | 600/443 |
| 2005/0215897 | A1 * | 9/2005 | Sakaguchi et al. | 600/437 |
| 2006/0079782 | A1 * | 4/2006 | Beach et al. | 600/450 |
| 2006/0100520 | A1 * | 5/2006 | Mo et al. | 600/457 |
| 2006/0264759 | A1 * | 11/2006 | Moehring et al. | 600/469 |
| 2007/0149879 | A1 * | 6/2007 | Roundhill et al. | 600/447 |
| 2008/0234580 | A1 * | 9/2008 | Bruce et al. | 600/441 |
| 2008/0242982 | A1 * | 10/2008 | Tamura | 600/441 |
| 2008/0269612 | A1 * | 10/2008 | Kunita | 600/455 |
| 2009/0015587 | A1 | 1/2009 | Hashimoto et al. | |
| 2009/0024029 | A1 * | 1/2009 | Murashita | 600/437 |
| 2009/0024033 | A1 * | 1/2009 | Murashita | 600/443 |
| 2009/0069675 | A1 * | 3/2009 | Srinivasan | 600/437 |
| 2009/0171206 | A1 | 7/2009 | Imamura et al. | |
| 2009/0304246 | A1 * | 12/2009 | Walker et al. | 382/128 |
| 2009/0306503 | A1 * | 12/2009 | Srinivasan et al. | 600/441 |
| 2009/0306513 | A1 * | 12/2009 | Srinivasan et al. | 600/454 |
| 2010/0286522 | A1 * | 11/2010 | Beach et al. | 600/441 |
| 2010/0331701 | A1 * | 12/2010 | Hamada | 600/454 |
| 2011/0015526 | A1 * | 1/2011 | Tamura | 600/453 |

FOREIGN PATENT DOCUMENTS

| | | |
|---|---|---|
| KR | 10-0352639 B1 | 8/2002 |
| KR | 10-2010-0119496 A | 11/2010 |

OTHER PUBLICATIONS

Korean Intellectual Property Office Notice of Allowance issued in Application No. 10-2010-0116920 with issue date Aug. 28, 2013 with English Translation.

Non-Final Office Action issued in corresponding Japanese Patent Application No. 2011-254034, mailed on Sep. 15, 2015; with English translation.

* cited by examiner

PROVIDING COLOR DOPPLER IMAGE BASED ON QUALIFICATION CURVE INFORMATION IN ULTRASOUND SYSTEM

CROSS-REFERENCE TO RELATED APPLICATIONS

The present application claims priority from Korean Patent Application No. 10-2010-0116920 filed on Nov. 23, 2010, the entire subject matter of which is incorporated herein by reference.

TECHNICAL FIELD

The present disclosure generally relates to ultrasound systems, and more particularly to providing a color Doppler image based on qualification curve information corresponding to characteristics of Doppler signals in an ultrasound system.

BACKGROUND

An ultrasound system has become an important and popular diagnostic tool since it has a wide range of applications. Specifically, due to its non-invasive and non-destructive nature, the ultrasound system has been extensively used in the medical profession. Modern high-performance ultrasound systems and techniques are commonly used to produce two-dimensional or three-dimensional ultrasound images of internal features of a target object (e.g., human organs).

The ultrasound system may provide ultrasound images of various modes including a brightness mode (B mode) image representing reflection coefficients of the ultrasound signals reflected from a target object of a living body with a 2D (two-dimensional) image, a Doppler mode (D mode) image representing speed of a moving target object with spectral Doppler by using a Doppler effect, a color Doppler mode (C mode) image representing speed of a moving target object with colors by using the Doppler effect, and an elastic mode (E mode) image representing mechanical characteristics of tissues object before and after applying a pressure thereto. Particularly, the ultrasound system may transmit and receive ultrasound signals to and from the living body to thereby form Doppler signals corresponding to a region of interest (ROI), which is set on a B mode image. The ultrasound system may further form a C mode image that represents the speed of the moving target object such as blood flow, heart, etc. with colors based on the Doppler signals.

The color Doppler image may be formed based on Doppler signals obtained by alternately transmitting and receiving ultrasound signals to and from a target object. The Doppler signals may include a low frequency signal (so-called clutter signals) due to the motion of a cardiac wall or valve of a heart. The clutter signals may have amplitude, which is over 100 times than that of the blood flow signals indicative of velocities of the blood flow. The clutter signals may be an obstacle for accurately detecting a velocity of the blood flow. Thus, it is required to remove the clutter signals from the Doppler signals for an accurate velocity detection of the blood flow.

The ultrasound system typically adopts a clutter filter that may be a high pass filter to remove the clutter signals from the Doppler signals. However, this presents a problem since the clutter filter cannot completely remove the clutter signals from the Doppler signals.

SUMMARY

There are provided embodiments for providing a color Doppler image based on qualification curve information corresponding to characteristics of Doppler signals in an ultrasound system.

In one embodiment, by way of non-limiting example, an ultrasound system comprises: an ultrasound data acquisition unit configured to acquire ultrasound data corresponding to a living body including a moving target object; a storage unit for storing qualification curve information for determining blood flow signals of the target object, clutter signals and noise based on velocity and power components of Doppler signals; and a processing unit configured to form first Doppler signals based on the ultrasound data, perform a clutter filtering process upon the first Doppler signals to form second Doppler signals, calculate velocity and power components of the second Doppler signals, form a color Doppler image based on the calculated velocity and power components, and perform a blending process upon the color Doppler image based on the calculated velocity and power components and the qualification curve information.

In another embodiment, there is a method of providing a color Doppler image, comprising: a) acquiring ultrasound data corresponding to a living body including a moving target object; b) forming first Doppler signals based on the ultrasound data; c) performing a clutter filtering process upon the first Doppler signals to form second Doppler signals; d) calculating velocity and power components of the second Doppler signals; e) forming a color Doppler image based on the calculated velocity and power components; and f) performing a blending process upon the color Doppler image based on the calculated velocity and power components and qualification curve information for determining blood flow signals of the target object, clutter signals and noise.

This summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
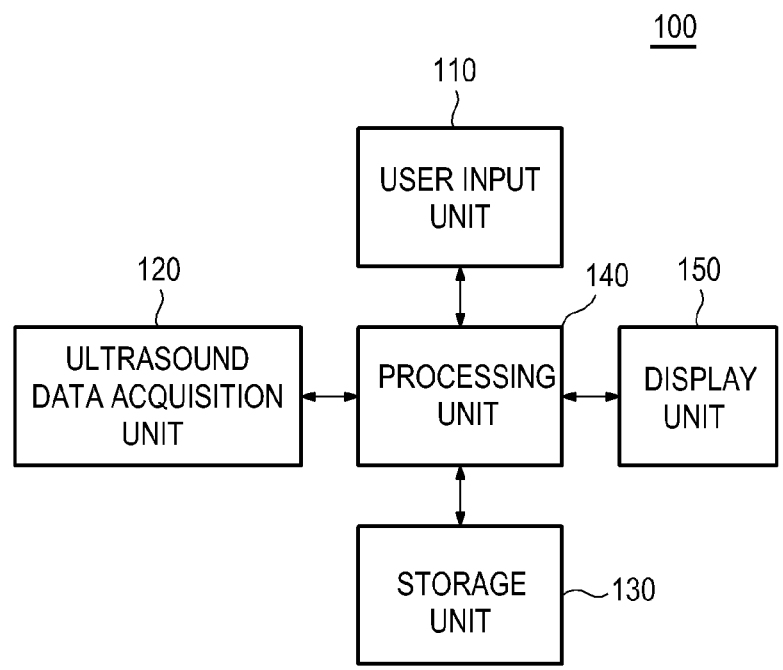
FIG. 1 is a block diagram showing an illustrative embodiment of an ultrasound system.

Referring to FIG. 1, an ultrasound system 100 in accordance with an illustrative embodiment is shown. As depicted therein, the ultrasound system 100 may include a user input unit 110.

Figure 2:
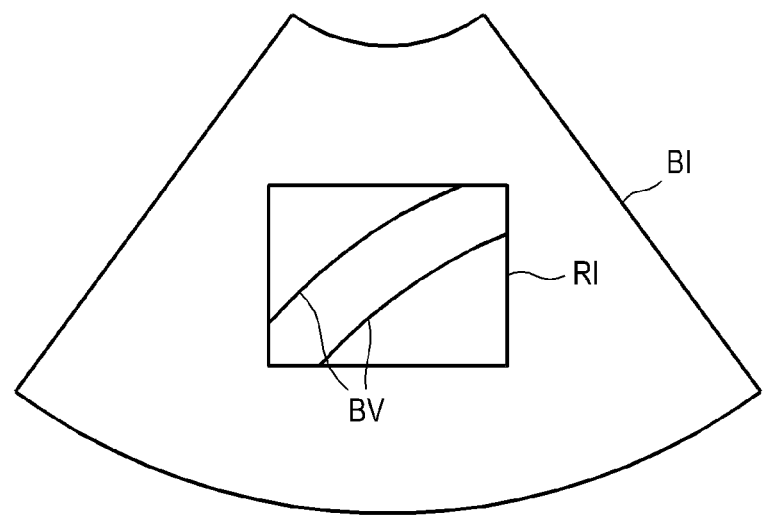
FIG. 2 is a schematic diagram showing an example of a brightness mode image and a region of interest.

The user input unit 110 may be configured to receive input information from a user. In the embodiment, the input information may include information for setting a region of interest RI on a brightness mode image BI, as shown in FIG. 2. However, it should be noted herein that the input information may not be limited thereto. The region of interest RI may include a color box for obtaining a color Doppler image. In FIG. 2, reference numeral BV represents a blood vessel. The user input unit 110 may include a control panel, a trackball, a mouse, a keyboard and the like.

The ultrasound system 100 may further include an ultrasound data acquisition unit 120. The ultrasound data acquisition unit 120 may be configured to transmit ultrasound signals to a living body and receive ultrasound signals (i.e., ultrasound echo signals) from the living body to acquire ultrasound data. The living body may include a periodically moving target object (e.g., blood flow, a heart, etc.).

Figure 3:
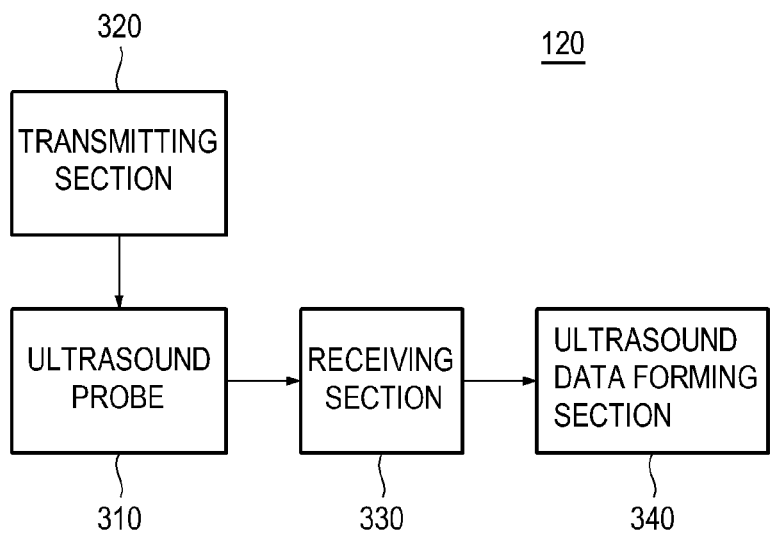
FIG. 3 is a block diagram showing an illustrative embodiment of an ultrasound data acquisition unit.
Figure 4:
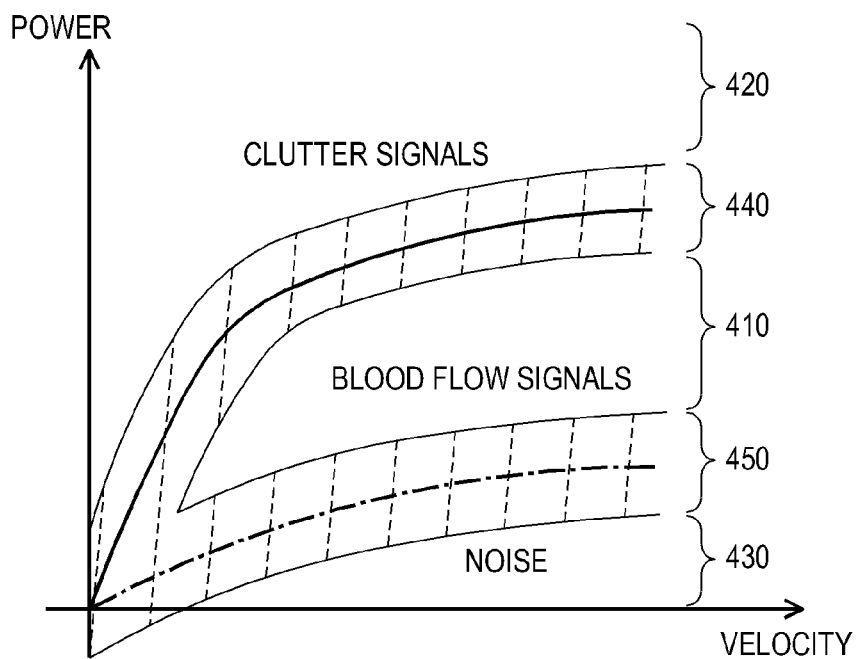
FIG. 4 is a schematic diagram showing an example of qualification curve information.

FIG. 3 is a block diagram showing an illustrative embodiment of the ultrasound data acquisition unit. Referring to FIG. 3, the ultrasound data acquisition unit 120 may include an ultrasound probe 310.

The ultrasound probe 310 may include a plurality of elements (not shown) for reciprocally converting between ultrasound signals and electrical signals. The ultrasound probe 310 may be configured to transmit the ultrasound signals to the living body. The ultrasound probe 310 may be further configured to receive the ultrasound echo signals from the living body to output received signals. The received signals may be analog signals. The ultrasound probe 310 may include a convex probe, a linear probe and the like.

The ultrasound data acquisition unit 120 may further include a transmitting section 320. The transmitting section 320 may be configured to control the transmission of the ultrasound signals. The transmitting section 320 may be further configured to generate electrical signals ("transmitting signals") for obtaining an ultrasound image in consideration of the elements and focusing points. Thus, the ultrasound probe 310 may convert the transmitting signals into the ultrasound signals, transmit the ultrasound signals to the living body and receive the ultrasound echo signals from the living body to thereby output the received signals. The transmitting section 320 may include a transmitting signal forming section (not shown), a transmitting delay time information memory (not shown), a transmitting beam former (not shown) and the like.

In the embodiment, the transmitting section 320 may generate first transmitting signals for obtaining the brightness mode image BI. Thus, the ultrasound probe 310 may convert the first transmitting signals into the ultrasound signals, transmit the ultrasound signals to the living body and receive the ultrasound echo signals from the living body to thereby output first received signals. The transmitting section 320 may further generate second transmitting signals for obtaining the color Doppler image corresponding to the region of interest RI based on a predetermined ensemble number. Thus, the ultrasound probe 310 may convert the second transmitting signals into the ultrasound signals, transmit the ultrasound signals to the living body and receive the ultrasound echo signals from the living body to thereby output second received signals. The ensemble number may represent the number of transmitting and receiving the ultrasound signals needed to acquire Doppler signals corresponding to a scanline.

The ultrasound data acquisition unit 120 may further include a receiving section 330. The receiving section 330 may be configured to convert the received signals provided from the ultrasound probe 310 into digital signals. The receiving section 330 may be further configured to apply delays to the digital signals in consideration of the elements and the focusing points to thereby output digital receive-focused signals. The receiving section 330 may include an analog-to-digital converter (not shown), a receiving delay time information memory (not shown), a receiving beam former (not shown) and the like.

In the embodiment, the receiving section 330 may convert the first received signals provided from the ultrasound probe 310 into first digital signals. The receiving section 330 may further apply delays to the first digital signals in consideration of the elements and the focusing points to thereby output first digital receive-focused signals. The receiving section 330 may further convert the second received signals provided from the ultrasound probe 310 into second digital signals. The receiving section 330 may further apply delays to the second digital signals in consideration of the elements and the focusing points to thereby output second digital receive-focused signals.

The ultrasound data acquisition unit 120 may further include an ultrasound data forming section 340. The ultrasound data forming section 340 may be configured to form ultrasound data corresponding to the ultrasound image based on the digital receive-focused signals provided from the receiving section 330. The ultrasound data forming section 340 may be further configured to perform a signal process (e.g., gain control, etc) upon the digital receive-focused signals.

In the embodiment, the ultrasound data forming section 340 may form first ultrasound data corresponding to the brightness mode image BI based on the first digital receive-focused signals provided from the receiving section 330. The first ultrasound data may include radio frequency data. However, it should be noted herein that the first ultrasound data may not be limited thereto. The ultrasound data forming section 340 may further form second ultrasound data corresponding to the color Doppler image based on the second digital receive-focused signals provided from the receiving section 330. The second ultrasound data may include the radio frequency data or in-phase/quadrature data. However, it should be noted herein that the second ultrasound data may not be limited thereto.

Referring back to FIG. 1, the ultrasound system 100 may further include a storage unit 130. The storage unit 130 may store the ultrasound data (i.e., first ultrasound data and second ultrasound data) acquired by the ultrasound data acquisition unit 120. The storage unit 130 may further store qualification curve information corresponding to the characteristics of Doppler signals.

In the embodiment, the storage unit 130 may store the qualification curve information for determining Doppler signals (hereinafter, "blood flow signals") by the blood flow, clutter signals by a motion of a blood vessel wall, and a noise from the Doppler signals based on velocity and power components of the Doppler signals. For example, the qualification curve may be a curve for determining a first region 410 corresponding to the blood flow signals, a second region 420 corresponding to the clutter signals, a third region 430 corresponding to the noise, a fourth region 440 that the blood flow signals and the clutter signals intermingle, and a fifth region 450 that the blood flow signals and the noise intermingle.

The ultrasound system 100 may further include a processing unit 140 in communication with the user input unit 110, the ultrasound data acquisition unit 120 and the storage unit 130. The processing unit 140 may include a central processing unit, a microprocessor, a graphic processing unit and the like.

Figure 5:
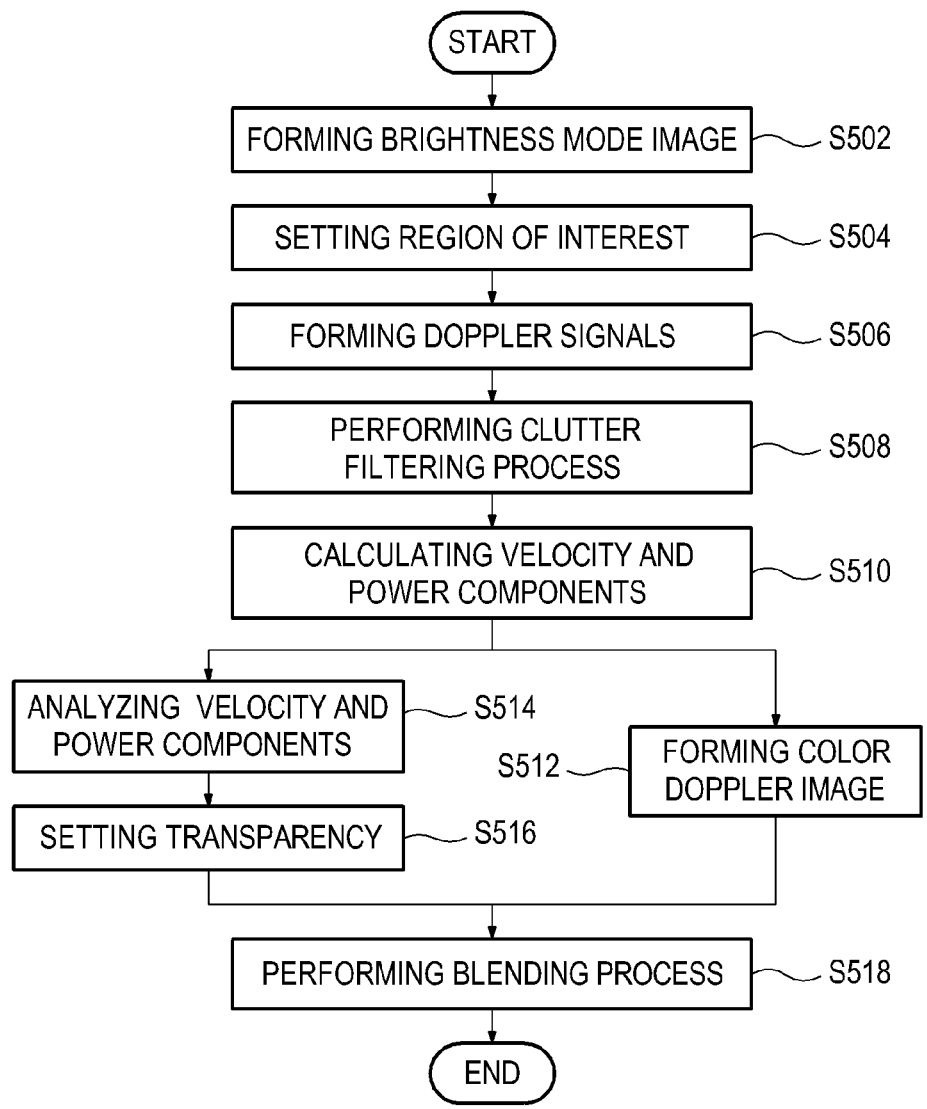
FIG. 5 is a flow chart showing a process of forming a color Doppler image.

FIG. 5 is a flow chart showing a process of forming the color Doppler image. The processing unit 140 may be configured to form the brightness mode image BI based on the first ultrasound data provided from the ultrasound data acquisition unit 120, at step S502 in FIG. 5. The brightness mode image BI may be displayed on a display unit 150. Thus, the user may set the region of interest RI on the brightness mode image BI by using the user input unit 110.

The processing unit 140 may be configured to set the region of interest RI on the brightness mode image BI based on the input information provided from the user input unit 110, at step S504 in FIG. 5. Thus, the ultrasound data acquisition unit 120 may acquire the second ultrasound data corresponding to the region of interest RI.

The processing unit 140 may be configured to form Doppler signals (hereinafter, "first Doppler signals) based on the second ultrasound data provided from the ultrasound data acquisition unit 120, at step S506 in FIG. 5. The first Doppler signals may include the blood flow signals by the blood flow, the clutter signals by the motion of the blood vessel wall and the noise.

The processing unit 140 may be configured to perform a clutter filtering process upon the first Doppler signals to form the clutter-filtered Doppler signals (hereinafter, "second Doppler signals"), at step S508 in FIG. 5. The methods of performing the clutter filtering process are well known in the art. Thus, they have not been described in detail so as not to unnecessarily obscure the present invention.

The processing unit 140 may be configured to calculate velocity and power components of the second Doppler signals, at step S510 in FIG. 5. The methods of calculating the velocity and power components are well known in the art. Thus, they have not been described in detail so as not to unnecessarily obscure the present invention.

The processing unit 140 may be configured to form the color Doppler image based on the calculated velocity and power components, at step S512 in FIG. 5. The methods of forming the color Doppler image are well known in the art. Thus, they have not been described in detail so as not to unnecessarily obscure the present invention.

The processing unit 140 may be configured to analyze the calculated velocity and power components based on the qualification curve information stored in the storage unit 130 to form qualification analysis information, at step S514 in FIG. 5. In the embodiment, the processing unit 140 may detect a region corresponding to the calculated velocity and power components among the first to fifth regions 410 to 450 of the qualification curve information, and form the qualification analysis information including the detected region.

Figure 6:
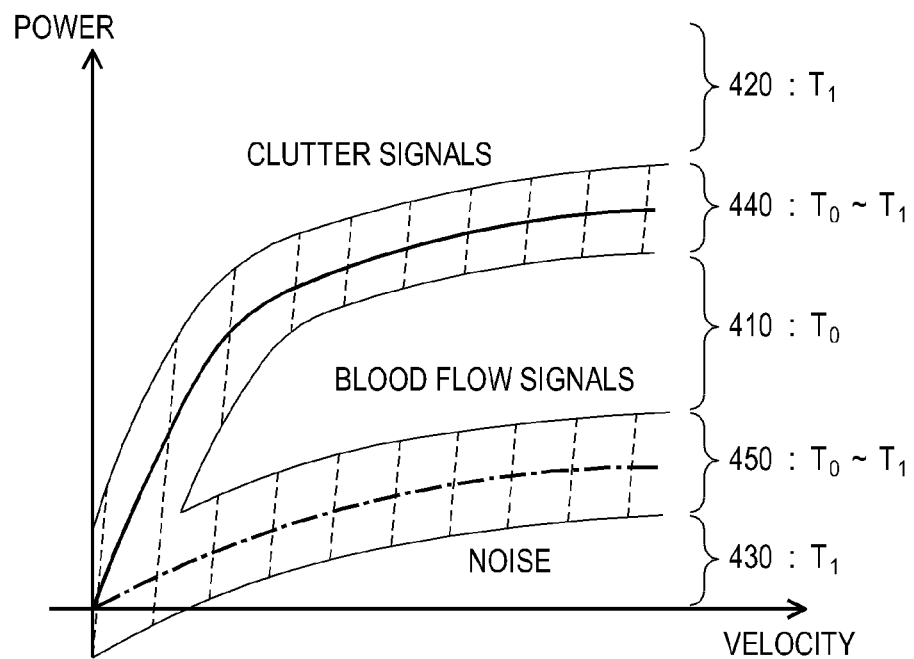
FIG. 6 is a schematic diagram showing an example of transparency.

The processing unit 140 may be configured to set transparency of the color Doppler image based on the qualification analysis information, at step S516 in FIG. 5. For example, the processing unit 140 may set first transparency $T_0$ of the color Doppler image based on the qualification analysis information that detected region is the first region 410 of the qualification curve information, as shown in FIG. 6. The first transparency $T_0$ may be 0. However, it should be noted herein that the first transparency may not be limited thereto. The processing unit 140 may further set second transparency $T_1$ of the color Doppler image based on the qualification analysis information that the detected region is the second region 420 or the third region 430 of the qualification curve information, as shown in FIG. 6. The second transparency $T_1$ may be 1.

However, it should be noted herein that the second transparency may be not limited thereto. The processing unit 140 may further set third transparency of the color Doppler image based on the qualification analysis information that the detected region is the fourth region 440 or the fifth region 450 of the qualification curve information, as shown in FIG. 6. The third transparency may be transparency between the first transparency $T_0$ and the second transparency $T_1$ (i.e., 0<third transparency<1). That is, the processing unit 140 may set the third transparency close to the first transparency $T_0$ as the calculated velocity and power components are closer to the first region 410, and set the third transparency close to the second transparency $T_1$ as the calculated velocity and power components are closer to the second region 420.

The processing unit 140 may be configured to perform a blending process upon the color Doppler image based on the transparency, at step S518 in FIG. 5. In the embodiment, the processing unit 110 may perform a transparency process upon the color Doppler image based on the transparency. The processing unit 140 may further compound the transparency-processed color Doppler image on the region of interest RI set on the brightness mode image BI.

Referring back to FIG. 1, the ultrasound system 100 may further include the display unit 150. The display unit 150 may be configured to display the brightness mode image BI formed by the processing unit 140. The display unit 150 may be further configured to display the color Doppler image formed by the processing unit 140.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
an ultrasound data acquisition unit including a probe configured to acquire ultrasound data corresponding to a living body including a moving target object;
a storage unit configured to store qualification curve information, the qualification curve information including blood flow signals of the target object, clutter signals and noise based on velocity and power components of Doppler signals; and
a processing unit coupled to the ultrasound data acquisition unit and the storage unit, the processing unit including at least one of a central processing unit, a microprocessor, or a graphic processing unit, the processing unit configured to form first Doppler signals based on the ultrasound data, perform a clutter filtering process upon the first Doppler signals to form second Doppler signals, calculate velocity and power components of the second Doppler signals, form a color Doppler image based on the calculated velocity and power components, and perform a blending process upon the color Doppler image based on the calculated velocity and power components and the qualification curve information,
wherein the qualification curve information includes a qualification curve for determining a first region corresponding to the blood flow signals, a second region corresponding to the clutter signals, a third region corresponding to the noise, a fourth region comprising a portion of the blood flow signals region and a portion of the clutter signals region, and a fifth region comprising a portion of the blood flow signals region and a portion of the noise region, and wherein the processing unit is configured to:

set transparency of the fourth region different from transparency of the first region and the second region and transparency of the fifth region different from transparency of the first region and the third region in the color Doppler image based on the qualification curve information;

perform a transparency process upon the color Doppler image based on the transparency of the fourth region and the transparency of the fifth region;

detect a region corresponding to the calculated velocity and power components among the first to fifth regions of the qualification curve information;

form qualification analysis information including the detected region; and perform the blending process based on the qualification analysis information.

2. The ultrasound system of claim 1, wherein the processing unit is configured to:

set the transparency of the color Doppler image as a first value based on the qualification analysis information when the detected region is the first region;

set the transparency of the color Doppler image as a second value based on the qualification analysis information when the detected region is the second region or the third region; and set the transparency of the color Doppler image as a third value based on the qualification analysis information when the detected region is the fourth region or the fifth region.

3. The ultrasound system of claim 2, wherein the first value is 0, the second value is 1, and the third value is a value between the first value and the second value.

4. The ultrasound system of claim 3, wherein the processing unit is configured to:

set the third value close to the first value as the calculated velocity and power components are closer to the first region, and set the third value close to the second value as the calculated velocity and power components are closer to the second region or the third region, based on the qualification analysis information that the detected region is the fourth or fifth region.

* * * * *